United States Patent [19]
Horrobin et al.

[11] Patent Number: 5,552,150
[45] Date of Patent: Sep. 3, 1996

[54] COMPOSTIONS CONTAINING DI-LINOLEOYL-MONO-GAMMA-LINOLENYL-GLYCEROL

[75] Inventors: David F. Horrobin, Guildford, England; Yung-Sheng Huang, Kentville, Canada

[73] Assignee: Efamol Holdings PLC, England

[21] Appl. No.: 158,986

[22] Filed: Nov. 30, 1993

Related U.S. Application Data

[62] Division of Ser. No. 891,037, Jun. 1, 1992, Pat. No. 5,328,691.

[30] Foreign Application Priority Data

Jun. 3, 1991 [GB] United Kingdom .................. 9111900

[51] Int. Cl.$^6$ ................ A61K 31/20; A61K 9/14; A61K 47/12
[52] U.S. Cl. .................. 424/439; 424/401; 424/422; 424/430; 424/435; 424/436; 424/443; 424/449; 424/451; 424/464; 424/489; 424/47; 424/78.03; 514/558
[58] Field of Search ..................... 424/401, 422, 424/430, 435, 436, 439, 443, 449, 451, 464, 489, 47, 78.03; 514/558

[56] References Cited

U.S. PATENT DOCUMENTS

| | | | |
|---|---|---|---|
| 4,172,149 | 10/1979 | Pinto et al. | 514/547 |
| 4,703,060 | 10/1987 | Traitler et al. | 514/549 |
| 4,888,326 | 12/1989 | Horrobin | 514/27 |
| 4,938,984 | 7/1990 | Traitler et al. | 426/580 |
| 4,970,076 | 11/1990 | Horrobin | 424/456 |
| 5,011,855 | 4/1991 | Traitler et al. | 514/558 |
| 5,116,624 | 5/1992 | Horrobin et al. | 424/702 |
| 5,116,871 | 5/1992 | Horrobin et al. | 514/560 |
| 5,145,686 | 9/1992 | Horrobin et al. | 424/677 |

FOREIGN PATENT DOCUMENTS

| | | |
|---|---|---|
| 0211502B1 | 2/1987 | European Pat. Off. . |
| 0218460B1 | 4/1987 | European Pat. Off. . |
| 0266323 | 5/1988 | European Pat. Off. . |
| 0271909 | 6/1988 | European Pat. Off. . |
| 0319360 | 6/1989 | European Pat. Off. . |
| 0115419B1 | 4/1992 | European Pat. Off. . |
| 2569347 | 2/1986 | France . |
| 2942021A1 | 4/1981 | Germany . |
| 2084172 | 4/1982 | United Kingdom . |
| 2181349 | 4/1987 | United Kingdom . |

OTHER PUBLICATIONS

Abstract of EP 454102.
Biosis No. 86106491 Nissen 90 (7) 1988 268–271 Fett Wissenschaft Technologie "Influence of polyunsaturated . . . ".
Biosis No. 86073414 Bordoni Drugs Exp Clin Res 14 (4) 1988 291–298 "Drugs under Experimental . . . Research".
Biosis No: 86073413 Biagi 14 (4) 1988 285–290 "Drugs under Experimental and Clinical Research".
Chemical Abstract CA: 113(21)190022f Hoshita "Fatty Acid Composition in oily health foods".
Biosis No: 95065215 Raederstorff Lipids 27 (12) 1992 1018–1023 "Borage or Primrose Oil etc".
Biosis No. 93114673 Huang Lipids 27 (2) 1992 104–110 "Effect of Maternal Dietary Fats etc".

*Primary Examiner*—Carlos Azpuru
*Attorney, Agent, or Firm*—Nixon & Vanderhye

[57] ABSTRACT

A natural or synthetic glycerol oil which comprises at least 20% by weight, preferably at least 25% of di-linoleoyl-mono-gamma-linolenyl-glycerol (DLMG), is used to supplement foods, nutritional compositions and in skin and hair care compositions.

4 Claims, No Drawings

COMPOSITIONS CONTAINING DI-LINOLEOYL-MONO-GAMMA-LINOLENYL-GLYCEROL

This is a divisional of application Ser. No. 07/891,037, filed Jun. 1, 1992, now U.S. Pat. No. 5,328,691.

Gamma-linolenic acid (GLA, 18:3 n-6) is of particular interest in nutrition, in skin care and in the treatment of various diseases. GLA is a normal intermediate in human metabolism. It is derived by delta-6-desaturation from the essential fatty acid (EFA) linoleic acid, which is found in substantial amounts in most diets. The conversion path, showing common enzymes with the n-3 series of EFAs, is:

TABLE 1

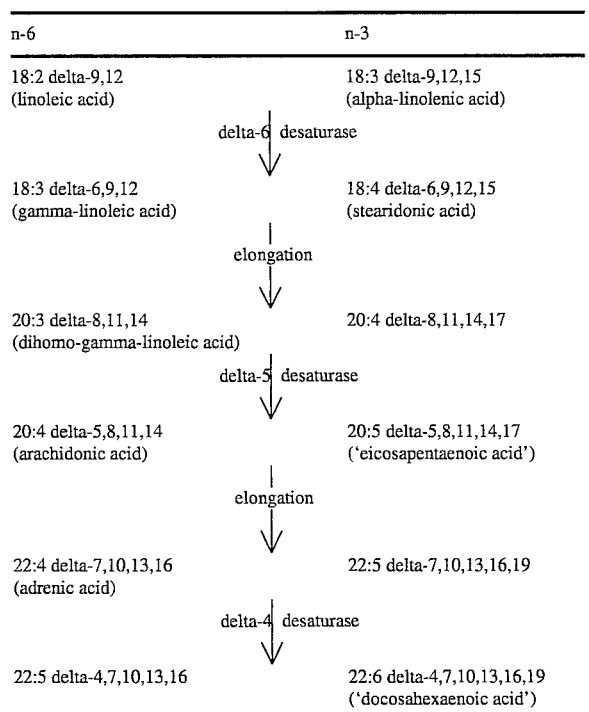

| n-6 | n-3 |
|---|---|
| 18:2 delta-9,12 (linoleic acid) | 18:3 delta-9,12,15 (alpha-linolenic acid) |
| 18:3 delta-6,9,12 (gamma-linoleic acid) | 18:4 delta-6,9,12,15 (stearidonic acid) |
| 20:3 delta-8,11,14 (dihomo-gamma-linoleic acid) | 20:4 delta-8,11,14,17 |
| 20:4 delta-5,8,11,14 (arachidonic acid) | 20:5 delta-5,8,11,14,17 ('eicosapentaenoic acid') |
| 22:4 delta-7,10,13,16 (adrenic acid) | 22:5 delta-7,10,13,16,19 |
| 22:5 delta-4,7,10,13,16 | 22:6 delta-4,7,10,13,16,19 ('docosahexaenoic acid') |

The above pathways are not normally reversible nor, in man, are n-3 and n-6 series acids inter-convertible.

The acids, which in nature are of the all-cis configuration, are systematically named as derivatives of the corresponding octadecanoic, eicosanoic or docosanoic acids, eg. delta-9, 12-octadecadienoic acid or delta-4, 7, 10, 13, 16, 19 docosahexaenoic acid, but numerical designations such as, correspondingly, 18:2 n-6 or 22:6 n-3 are convenient. Initials, for example, EPA for the 20:5 n-3 acid (eicosapentaenoic acid) or DHA for the 22:6 n-3 acid (docosahexaenoic acid), are also used but do not serve when n-3 and n-6 acids of the same chain length and degree of unsaturation exist as for example with the 22:5 acids. Trivial names in more or less common use in the n-6 series are as shown. Of the n-3 series only 18:3 n-3 has a commonly used trivial name, alpha-linolenic acid, though the name stearidonic acid is coming into use for the 18:4 n-3 acid and the names eicosapentaenoic acid and docosahexanenoic acid as such are also used. The alpha isomer of linolenic acid was characterised earlier than gamma-linolenic acid and reference in the literature simply to linolenic acid, especially in the earlier literature, is to the alpha-acid.

As is clear from the above, linoleic acid (LA) is an essential nutrient which, like a vitamin, cannot be made within the body and so must be taken in the diet. However, in order to be fully useful to the body, LA must be metabolised, first to GLA and then to further metabolites.

LA has some functions which it can perform itself, particularly in the skin and other membranes and in relation to cholesterol transport, but many of its effects require conversion to GLA and beyond. The GLA and the further metabolites each appear to have particular roles in the body and so this first metabolic step is of particular significance. Its importance is emphasised by the fact that it seems vulnerable to blockade in a number of situations. For example, ageing, high cholesterol levels, high alcohol intake, certain viral infections, atopic eczema, breast pain, diabetic neuropathy and certain forms of cancer all appear to be associated with a reduced ability to make GLA. In these situations, and in any other situation associated with a rate of GLA formation inadequate to supply the body's needs, it may be advantageous to provide GLA directly.

Useful sources of GLA are relatively few. GLA is found in moderate amounts in human breast milk, but that is clearly not a practical commercial source. GLA can be synthesised with some difficulty and it is possible that the known synthetic routes could be improved, or entirely new ones found. A number of plant oils contain GLA, the most important known examples to date being the seed oils from the evening primrose (Oenothera spp), from borage (*Borago officinalis*) and from members of the Ribes family such as blackcurrants. Some fungi and algae form GLA-rich lipid stores, examples being strains of Rhizopus, Mortierella, Mucor and Spirulina.

The seed oil of the evening primrose (EPO) has been widely used commercially as a component of foods, as a nutritional supplement, as an ingredient of cosmetic, skin care and hair care products, and as a pharmaceutical. For example, it is used in Japan for addition to artificial infant milks to make them more like breast milk, while in the United Kingdom and some other countries it is approved as a prescription drug for the treatment of atopic eczema and of breast pain. In many countries throughout the world it is used as a nutritional supplement and as a skin product ingredient.

However, EPO contains only 8 to 10% of its fatty acids as GLA. It has therefore been suggested that other sources such as borage oil, which may contain over 20% of GLA, or blackcurrant or fungal oils which may contain in the region of 15 to 25% of GLA may provide better sources. However, it has somewhat surprisingly been found that clinically these oils appear to be less effective than evening primrose oil, or not as effective as would be expected given their GLA content. May patients who have experienced a clinical response to EPO, for example in the case of atopic eczema or pre-menstrual breast pain, have relapsed on switching to one of the other GLA sources, even though the amount of GLA consumed may be greater. Biological testing has subsequently shown that equal amounts of GLA may indeed have very different effects when that GLA is supplied as different oil sources.

One of the most important biological consequences of administering GLA is its conversion within the body, first to dihomo-gamma-linolenic acid (DGLA) and then to prostaglandin (PGE1). PGE1 has a wide range of desirable effects, including being anti-inflammatory, vasoctilator, anti-thrombotic, cholesterol-lowering and anti-hypertensive, and its relation to the n-6 series EFAs is shown in the following chart:

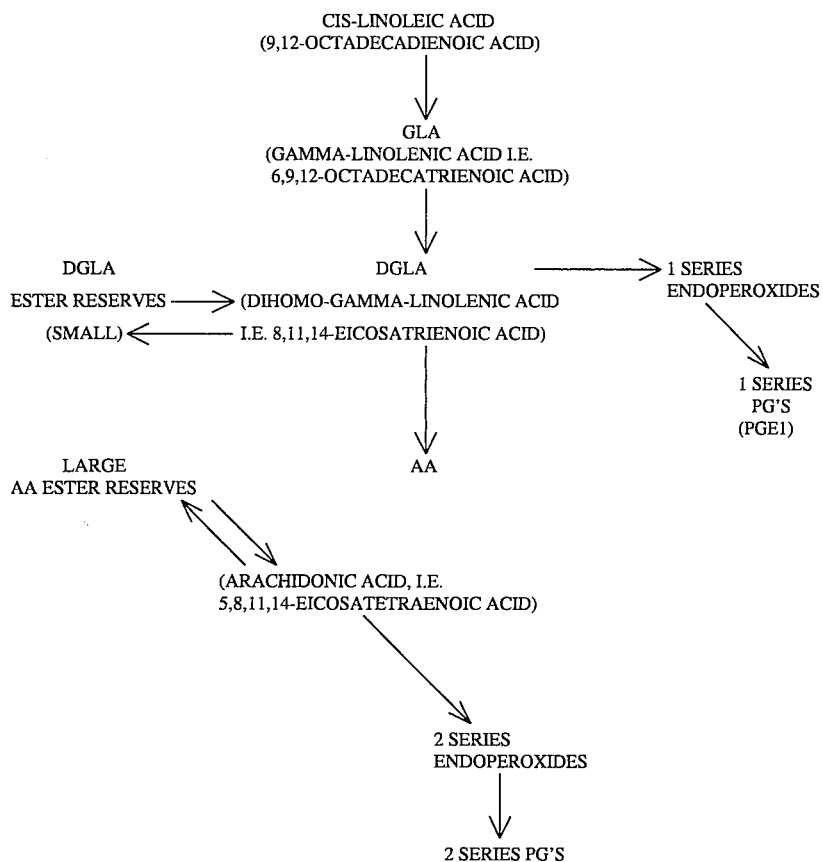

In order to test their ability to stimulate the formation of PGE1, EPO, borage oil, blackcurrant oil and microbial oil were fed to laboratory rats in amounts which provided the same daily dose of GLA. After the same period on the diet, the mesenteric vascular bed was removed from the animals and its rate of production of PGE1 while being perfused with oxygenated buffer was measured. The results are shown in Table 2.

TABLE 2

Amounts of PGE1 in ng/hour produced by the perfused superior mesenteric vascular bed of rats fed with equal amounts of GLA per day in the form of evening primrose, fungal, blackcurrant or borage oils.

| Oil | PGE1 outflow |
| --- | --- |
| Evening primrose | 14 |
| Fungal | 6 |
| Blackcurrant | 2 |
| Borage | 1 |

As can be seen, EPO was much more effective than the ether oils at increasing PGE1 outflow and since this effect of EPO is obviously not simply related to the amount of GLA in the oil, it seemed to us that it might depend on the detailed tri-glyceride structure of the oil. Fatty acids in vegetable oils are present not as the free fatty acids themselves hut primarily as components of triglycerides, a glycerol backbone

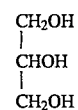

with three fatty acids attached to it by ester links. It seemed to us possible that there might be a particular triglyceride (TG) present in EPO which happened to be there in much larger quantities than in the other oils, and that this TG might account for the desirable biological effects of EPO. We therefore quantitated the amounts of the various triglycerides present in each of the common sources of GLA, with results set out in Table 3 appended to this specification.

The TGs in the oils were separated by reverse phase high pressure liquid chromatography (HPLC). We initially synthesised four triglycerides, tri-gamma-linolenyl-glycerol (tri-GLA), tri-linoleoyl-glycerol (tri-LA), mono-linoleoyl-di-gamma-linolenyl-glycerol (mono-LA-di-GLA) and di-linoleoyl-mono-gamma-linolenyl-glycerol (DLMG). These were used to optimise the conditions for analysis. The TGs were dissolved in chloroform and then applied to a Beckman System Gold (trade mark) programmable solvent module 126, with two identical 250 mm reverse phase columns (Supelcosil LC-18 (trade mark)) connected in series to increase the resolution of the highly unsaturated TG species. The eluted TG fractions were detected by a mass (light scattering) detector supplied by Applied Chromatography Systems, Macclesfield, England. Each fraction was collected manually. Each fraction was then mixed with a known amount of internal standard (tri-heptadecanoin) and the methyl esters of the fatty acids were generated using $BF_3$-methanol. The fatty acid methyl esters were then analysed by gas chromatography using a 50 m fused silica capillary column (Supelcomega (trade mark)) in an HP 5890 gas chromatograph equipped with a flame ionisation detector. This technique clearly separates the triglyceride fractions and then identifies the fatty acids present in each fraction but it does not identify the positions of the fatty acids in the TG molecule.

Using this technique, thirty five peaks were identified in borage oil, with the early peaks which contained the highly unsaturated fatty acids being very clearly separated. There were only eighteen readily identifiable peaks in EPO. Blackcurrant and fungal oils which contain more fatty acids than EPO or borage oil contained many more peaks. Table 3 shows all the identified peaks in EPO and borage oil.

Inspection of the table shows one particular GLA-containing fraction which is present at a high level in EPO but at a lower level in borage oil, the amount in EPO being substantially greater than the amount present in borate, with even lower levels in fungal and blackcurrant oils. This fraction contains two moieties of linoleic acid and one of GLA (di-linoleoyl-mono-gamma-linolenyl-glycerol, (DLMG)). No other GLA-containing peak shows such an obvious difference between the four oils. DLMG makes up 18 to 19% of the triglycerides in EPO, smaller amounts of those in borage oil, and much smaller amounts in fungal or blackcurrant oils.

We have synthesized DLMG with its GLA in the 2 position or in the 1 or 3 positions, and have found these molecules to be similar in their effects on elevated blood pressure in rats with spontaneous hypertension and on cholesterol levels in animals fed cholesterol. While there may be small differences in biological effects depending on the precise position of one GLA, it appears that the main beneficial effect relates to the presence of two linoleic acid moieties and one GLA moiety on the same triglyceride. This is thought to be because such a triglyceride will provide LA which is positioned before the rate-limiting delta-6 desaturase step in EFA metabolism, and GLA which comes after this step. Therefore, LGG, present at low levels in both EPO and borage oils is also expected to have desirable biological effects. It is also expected that some effect may also be seen using TG's having one LA, one GLA and a different, third fatty acid residue, such as OLG and PLG, but these are likely to be less valuable because of the presence of a moiety which has no essential fatty acid activity.

We therefore believe that it is the presence of DLMG which explains the usual biological potency of the GLA in EPO. This TG may have its GLA in either the 2 position or in the 1 or 3 positions in the triglyceride molecule, with linoleic acid occupying the other two positions.

Accordingly, the invention provides a triglyceride which is di-linoleoyl-mono-gamma-linolenyl glycerol (DLMG).

On this basis, and herein lies one aspect of the invention, any pharmacologically or nutritionally acceptable natural or synthetic glyceride oil selectively enriched in or supplemented with DLMG is, in view of the established value of GLA and the now-shown value of its presence as DLMG, a valuable and normal product both as such and in use in the preparation of a medicament or dietary composition for the purposes for which GLA is valuable.

GLA itself has extensive potential uses as a pharmaceutical and as a nutritional supplement. Many of these uses have been documented in previous patents and patent applications from the present applicants. These applications relate to the use of GLA and other EFA's in the treatment of a variety of disorders, including skin disorders such as atopic eczema, breast disorders including breast pain, premenstrual syndrome, psychiatric disorders including alcoholism, schizophrenia and Alzheimer's disease, cardiovascular disorders including the prevention and treatment of coronary heart disease, peripheral vascular disease and hypertension, disorders of inflammation including rheumatoid arthritis, osteoarthritis, inflammatory bowel disease, connective tissue disorders and related conditions, disorders of immunity including multiple sclerosis, Sjogren's syndrome, systemic sclerosis and related conditions, diabetes and in particular the long term complications of neuropathy, retinopathy, vascular disease and nephropathy, other renal diseases, disorders of calcium and bone metabolism including osteoporosis and excessive urinary calcium excretion, viral infections and post-viral fatigue syndrome, cancers, and the complications following radiotherapy for cancer and other disorders. Nutritional problems of particular importance include enteral and parenteral supplementation for infants, specialist infant formulae, supplements for the elderly, and supplements of various types for those with gastrointestinal problems and malabsorption. This list of potential applications for the invention is not exhaustive and is provided as an example of the possible utility of the invention.

Further, as far as we are aware, no evening primrose or other oil which has been used to date for nutritional, skin care, pharmaceutical or other purposes has contained more than 20% of DLMG. A further aspect of the invention is therefore an oil containing more than 20% by weight of DLMG, desirably more than 25 %, preferably more than 40%, very preferably more than 60%, more preferably more than 90% and ideally more than 98%. Such oils may be used in the preparation of a medicament or dietary composition for the above purposes, in which may be included:

(1). Oils to be added to or used with any type of food for humans or animals, including but not limited to margarines, modified butters, cheeses and cheese spreads, milks, yogurts, chocolates, chocolate bars and any other types of sweet or candy, snacks, salad oils, cooking oils, cooking fats, bakery products, pates, meats, fish and seafood products, infant milks and infant foods of all sorts, canned or bottled products such as whips or creams, solid forms such as powders or granules, drinks of any sort and cereals.

(2). Oils to be used in manufacturing any form of nutritional supplement preparation, including but not limited to hard or soft gelatin capsules (whether uncoated or for example enteric-coated), granules, tablets, draguees, pastilles, canned or bottled liquids, oils, whips, creams (whether or not in dosage-metered containers) or any other dosage form appropriate to a nutritional supplement, including ones for lingual or sub-lingual administration.

(3). Oils to be used in formulae for special nutritional purposes including foods and fluids for term and pre-term infants, enteral, parenteral, rectal, percutaneous compositions and foods or fluids for any appropriate route of administration.

(4). Oils to be used in the treatment of any disease in which GLA is beneficial by oral, lingual and sublingual, enteral, parenteral (sub-cutaneous, intramuscular, intra-venous, intra-peritoneal or other route), rectal, vaginal, percutaneous or other routes of administration. The oil may be contained in any of the dosage forms specified in (2) or in any other appropriate dosage form.

(5). Oils to be used in any preparation applied to the skin for the purpose of caring for normal skin or for treating rough, dry or ageing skin, or for treating injured or burned skin, or skin affected by any disease or trauma.

(6). Oils to be used in any preparation applied to the hair for the purpose of caring for normal hair, or for stimulating hair growth, or for treating thinning, damaged, dry or greasy hair, or for treating hair or the scalp affected by any disease. Preferred oils according to the invention comprise at least 20% by weight of DLMG.

The oils may be prepared by any method. The following are some examples but do not exclude the use of other methods.

i. Any natural oil containing DLMG, especially EPO, but also borage, blackcurrant or other plant oils, and microbial oils, may be treated to separate out the DLMG. The separated DLMG may be used to enhance or supplement any oil, natural or synthetic, to make a product containing 20%, desirably 25% or more DLMG. Such separation techniques include, but are not limited to low temperature precipitation of less polyunsaturated triglycerides figs), enzymic digestion using specific enzymes for TGs other than DLMG, differential solution using solvents of more or less polyunsaturated TGs, or chromatography techniques using appropriate column conditions, packing, temperatures and pressures and solvents.

ii. Any natural oil whether known or unknown to date, or developed from known plants such as Oenothera or other appropriate species by plant breeding, genetic engineering or other techniques, which contains 20%, desirably 25% or more DLMG.

iii. Any oil made synthetically from GLA and LA. GLA and LA may be synthesised or prepared from any appropriate source. As examples, they may be made by hydrolysis of natural oils, followed by concentration of the GLA and/or LA by techniques known to those skilled in the an such as urea complexation, low temperature crystallisation, binding to materials such as zeolites which selectively concentrate poly-unsaturated fatty acids, differential solution in appropriate solvents selective for unsaturated or other fatty acids, or concentration using enzymes which are selective for particular fatty acids or groups of fatty acids. Appropriate mixtures of GLA or LA or any appropriate derivatives such as salts, alcohols, amides or other compounds, may then be converted to tri-glycerides by a range of different techniques known to those skilled in the art. Examples of such techniques include conventional organic synthesis, using for example zinc as a catalyst, or the use of the chlorides as starting materials, in an appropriate organic solvent with pyridine, or by using an appropriate enzyme system such as lipozyme IM20 (available from Novo) or by using chemical techniques developed for specific placement of GLA or any other fatty acid in a specific position in the tri-glyceride molecule. The DLMG or LGG resulting from such synthetic procedures can then be concentrated and purified as appropriate as outlined under (i) above.

It is to be understood that the concept of using DLMG and/or LGG for nutritional, pharmaceutical, skin care or other purposes is independent of the methods which may actually be used for making DLMG or LGG in appropriate forms.

EXAMPLES

1. An oil to be made available for use by food manufacturers containing 30%, 45%, 70%, 95% or 99% of DLMG.
2. An oil to be made available for use by manufacturers of skin care and hair care preparations containing 30%, 45%, 70%, 95% or 99% of DLMG.
3. Ampoules prepared for addition to enteral foods or to sterile lipid emulsions for intra-venous administration, each containing 10 or 20 ml of an oil containing 95% or 99% DLMG.
4. Enteral foods or infant foods containing 1%, 2%, 5% or 10% of an oil containing 30%, 45%, 70%, 95% or 99% of DLMG.
5. Skin care preparations containing 0.5%, 1%, 2%, 5% or 10% or 20% of an oil which contains 30%, 45%, 70%, 95% or 99% of DLMG.
6. Preparations as in (5) but for hair care or scalp care.
7. Oils for direct ingestion or for mixing with other foods such as salad oils containing 30%, 45%, 70%, 95% or 99% of DLMG.
8. Capsules for use as nutritional supplements containing 100 mg, 200 mg, 500 mg or 750 mg of an oil containing 25%, 50%, 75%, 90% or 99% DLMG.
9. Capsules as in (8) but for pharmaceutical use.
10. Whips, creams or other formulations contained in bottles, cans or other appropriate containers containing 2%, 5%, 10%, 20% or 50% of oils containing 25%, 50%, 75%, 95% or 99% DLMG.
11. Granules, tablets or powders made with dextran, agar, gum acacia, calcium salts or other appropriate vehicle containing oil containing 25%, 50%, 70%, 90% or 99% DLMG.
12. Formulations for lingual or sub-lingual administration containing oil containing 25%, 40%, 60%, 80%, or 99% DLMG.

TABLE 3

Triglyceride peaks found in evening primrose and borage oils. Eight peaks occur in both oils, ten in EPO only and twenty seven in borage only.

| Peak | Probable Identity | % in EPO | % borage oil |
|---|---|---|---|
| 1 | GGG | 0.19 | 0.29 |
| 2 | LGG | 2.00 | 2.87 |
| 3 | LLG | 18.47 | 5.33 |
| 4 | LGO/S/P | 0.70 | 1.71 |
| 5 | GL/O/S/P | 1.76 | — |
| 5a | GGP | — | 2.21 |
| 6 | LLL | 43.19 | 7.24 |
| 7 | OLG | 3.92 | 8.76 |
| 8 | PLG | 3.45 | 7.10 |
| 9 | LG/O/P/S | 3.75 | — |
| 9A | SGG | — | 0.79 |
| 10 | OLL | 10.61 | 7.50 |
| 11 | LLP | 8.23 | — |
| 11A | L20:1/G/0 | — | 3.55 |
| 12 | LSG/O/P | 1.36 | — |
| 12a | OLP/G | — | 7.25 |
| 13 | LPS/O/G | 0.20 | — |
| 13a | POG | — | 5.25 |
| 14 | LLO/S | 0.26 | — |
| 14a | PPG | — | 1.58 |
| 15 | LOO/S/P | 1.10 | — |
| 15a | LL20:1 | — | 2.68 |
| 16 | LOP/S | 3.67 | — |
| 16a | OLG/? | — | 5.50 |
| 17 | LLO/P/S | 0.07 | — |
| 17a | OLG/22:1 | — | 3.88 |
| 18 | LPO/S/G | 0.45 | — |
| 18a | LOS/P | — | 3.88 |
| 19 | LOP/G/20:1 | — | 1.65 |
| 20 | PG20:1 | — | 1.85 |
| 21 | PLS/G | — | 1.04 |
| 22 | PSG | — | 1.77 |
| 23 | LL22:1 | — | 1.43 |
| 24 | LG? | — | 2.74 |
| 25 | SL/G/22:1 | — | 1.50 |
| 26 | PL20:1 | — | 1.45 |
| 27 | LP/S/O/20:1 | — | 2.33 |
| 28 | OPL/G/S/22:1 | — | 0.59 |
| 29 | POG/L/S/20:1/22:1 | — | 1.08 |
| 30 | SP/L/G/20:1/22:1 | — | 0.43 |
| 31 | PSL | — | 1.20 |
| 32 | LL24:1 | — | 0.87 |

TABLE 3-continued

Triglyceride peaks found in evening primrose and borage oils.
Eight peaks occur in both oils, ten in EPO only and twenty seven in borage only.

| Peak | Probable Identity | % in EPO | % borage oil |
|------|-------------------|----------|--------------|
| 33 | LO22:1/20:1/S | — | 0.90 |
| 34 | SG20:1 | — | 0.88 |
| 35 | PG22:1 | — | 0.84 |

In the Table G = gamma-linolenic acid, L = linoleic acid, O = oleic acid, P = palmitic acid and S = stearic acid.
Fatty acids not underlined are the major components, usually making up to 25 to 40% of the peak, underlined fatty acids being present in the peak in smaller amounts. Fatty acids making up less than 5% of a peak are not identified. Pairs of peaks (e.g. 11 and 11a) elute at similar times but have different compositions in the two oils.

We claim:

1. A food additive, nutritional supplement or special food for infants; older children or adults which contains or has added thereto a natural or synthetic glycerol oil comprising at least 20% by weight of di-linoleoyl-mono-gamma-linolenyl-glycerol.

2. A food additive which contains or has added thereto a natural or synthetic glycerol oil comprising at least 20% by weight of di-linoleoyl-mono-gamma-linolenyl-glycerol, wherein the food additive is selected from the group consisting of margarines, modified butters, cheeses, cheese spreads, milks, yogurts, chocolates, chocolate bars, candy, snacks, salad oils, cooking oils, cooking fats, bakery products, pates, meats, fish, seafood products, infant milks, infant foods, canned products, bottled products, powders, granules, drinks and cereals.

3. A nutritional supplement which contains or has added thereto a natural or synthetic glycerol oil comprising at least 20% by weight of di-linoleoyl-mono-gamma-linolenyl-glycerol, wherein the nutritional supplement is selected from the group consisting of hard gelatin capsules, soft gelatin capsules, granules, tablets, draguees, pastilles, canned liquids, bottled liquids, oil, whips and creams.

4. An infant food which contains or has added thereto a natural or synthetic glycerol oil comprising at least 20% by weight of di-linoleoyl-mono-gamma-linolenyl-glycerol, wherein the infant food is a composition selected from the group consisting of fluids for term and pre-term infants, enteral compositions, parenteral compositions, rectal compositions and percutaneous compositions.

* * * * *